US010202338B2

(12) United States Patent
Weinberger et al.

(10) Patent No.: US 10,202,338 B2
(45) Date of Patent: Feb. 12, 2019

(54) TOPICAL COMPOSITIONS FOR THE TREATMENT OF DERMATOLOGICAL DISORDERS

(75) Inventors: Gary I. Weinberger, East Amherst, NY (US); H. Robert Nagel, Newton, MA (US); Richard A. Brown, Park City, UT (US)

(73) Assignee: Evologie LLC, Newton, MA (US)

( * ) Notice: Subject to any disclaimer, the term of this patent is extended or adjusted under 35 U.S.C. 154(b) by 134 days.

(21) Appl. No.: 14/126,275

(22) PCT Filed: Jun. 11, 2012

(86) PCT No.: PCT/US2012/041895
§ 371 (c)(1),
(2), (4) Date: Mar. 6, 2014

(87) PCT Pub. No.: WO2012/177433
PCT Pub. Date: Dec. 27, 2012

(65) Prior Publication Data
US 2014/0179640 A1  Jun. 26, 2014

Related U.S. Application Data

(60) Provisional application No. 61/499,523, filed on Jun. 21, 2011.

(51) Int. Cl.
*A61K 9/107* (2006.01)
*C07C 279/14* (2006.01)
*A61K 31/194* (2006.01)
*A61K 31/198* (2006.01)
*A61K 31/223* (2006.01)
*A61K 31/60* (2006.01)
*A61K 47/14* (2017.01)

(52) U.S. Cl.
CPC ............ *C07C 279/14* (2013.01); *A61K 9/107* (2013.01); *A61K 31/194* (2013.01); *A61K 31/198* (2013.01); *A61K 31/223* (2013.01); *A61K 31/60* (2013.01); *A61K 47/14* (2013.01)

(58) Field of Classification Search
CPC .................................................... A61K 9/107

USPC ......................................................... 514/159
See application file for complete search history.

(56) References Cited

U.S. PATENT DOCUMENTS

| 5,364,884 A | 11/1994 | Varma et al. |
| 5,871,754 A | 2/1999 | Briggs et al. |
| 6,143,310 A | 11/2000 | Sang et al. |
| 6,306,993 B1 | 10/2001 | Rothbard et al. |
| 6,335,023 B1 * | 1/2002 | Yu .................... A61K 8/0212 424/401 |
| 7,399,616 B2 | 7/2008 | Seguer Bonaventura et al. |
| 2003/0225119 A1 | 12/2003 | Souza et al. |
| 2004/0033963 A1 * | 2/2004 | Yu ....................... A61K 8/365 514/23 |
| 2004/0122258 A1 | 6/2004 | Amey et al. |
| 2004/0220264 A1 * | 11/2004 | Yu et al. .................. 514/554 |
| 2005/0226821 A1 | 10/2005 | Waugh et al. |
| 2009/0214452 A1 | 8/2009 | Waugh |
| 2009/0318557 A1 | 12/2009 | Stockel |
| 2010/0124576 A1 | 5/2010 | Amato et al. |
| 2010/0196517 A1 | 8/2010 | Fossel |

OTHER PUBLICATIONS

Vemula et al. (International Journal of Pharmaceutical Sciences Review and Research (2010), vol. 5 pp. 41-51).*
Kornhauser et al. (Clin Cosmet Investig Dermatol, vol. 3 (2010) pp. 135-142 (Year: 2010).*
International Search Report for International Application PCT/US2012/041895, dated Aug. 28, 2013.

* cited by examiner

*Primary Examiner* — Brandon J Fetterolf
*Assistant Examiner* — Taina D Matos Negron
(74) *Attorney, Agent, or Firm* — Sean D. Detweiler, Esq.; Stanley F. Chalvire; Morse, Barnes-Brown & Pendleton, P.C.

(57) ABSTRACT

The present invention relates to pharmaceutical compositions and methods useful for the treatment of dermatological disorders, and in particular acne vulgaris and skin pigmentation disorders. Pharmaceutical compositions comprising one or more arginine, salicylic acid and/or azelaic acid that are useful for the treatment of dermatological diseases and the symptoms and underlying causes of such dermatological diseases are also disclosed.

16 Claims, 1 Drawing Sheet

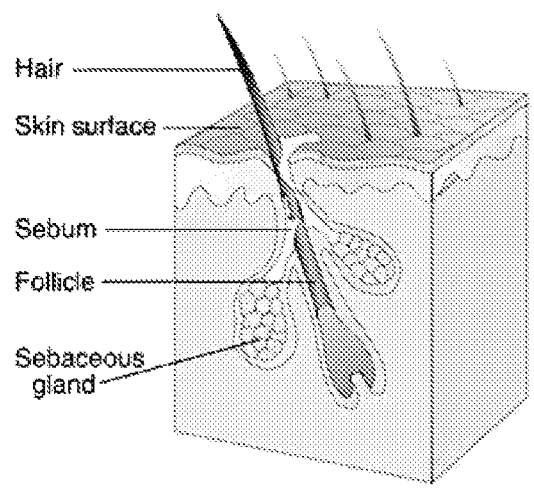
Normal Pilosebaceous Unit

TOPICAL COMPOSITIONS FOR THE TREATMENT OF DERMATOLOGICAL DISORDERS

RELATED APPLICATION

This application is a national stage filing under 35 U.S.C. 371 of International Application No. PCT/US 2012/041895, filed Jun. 11, 2012, which claims priority to U.S. Provisional Application No. 61/499,523 filed on Jun. 21, 2011, the entire teachings of which are incorporated herein by reference. International Application No. PCT/US2012/041895 was published under PCT Article 21(2) in English.

FIELD OF THE INVENTION

The present invention relates to pharmaceutical compositions and related methods of use thereof. In certain embodiments, the pharmaceutical compositions disclosed herein are topically applied and comprise one or more of arginine, salicylic acid and/or azelaic acid and are useful for the treatment of dermatological disorders, such as acne vulgaris and skin pigmentation disorders.

BACKGROUND OF THE INVENTION

Unwanted dermatological disorders often associated with the production or over production of sebum are well known. One such dermatological disorder includes acne vulgaris (acne), which is the most common dermatological disorder treated by physicians. It is estimated that as many as 32 million Americans exhibit some form of unwanted acne. Acne affects more than eighty-five percent of teenagers, and although acne most commonly occurs during adolescence, the condition may commonly continue into adulthood. (William, J., *N Engl J Med*, (2005) 352:1463-1472.)

Acne is an inflammatory dermatological disorder affecting the pilosebaceous units of affected subjects. Acne is cause by bacteria that infects the hair follicles, which in turn leads to the formation of comedones composed of sebum, keratin and further proliferation of microorganisms, which include for example, *Propionibacterium acnes* (*P. acnes* or *P. acneis*). It is further believed that *P. acnes* plays a role in the digestion of the sebum and keratin present in the comedones into inflammatory by-products which are responsible for further irritating the affected hair follicle, thereby resulting in further inflammation, the formation of abscesses or cysts, which in severe cases may lead to scarring.

In many affected subjects, acne scarring and/or post-inflammatory hyperpigmentation (PIH) occurs as a result of inflammation of the pilo-sebaceous unit (PSU), and in some cases the scarring can be permanent. Subjects affected by PIH generally present with irregular, darkly-pigmented spots occurring after inflammation due to a skin insult such as, for example acne. In some individuals PIH may resolve slowly but may persist for months. (Kenney, J., et al., *Clinics in Dermatology* (1989) 7:1-10; Grimes, P. et al., Dermatologic Clinics (1988) 6:271-81). Although the pathogenesis underlying PIH is relatively well-understood, available therapies for PIH remains unsatisfactory and currently available therapies, which include, for example the use of hydroquinones as bleaching agents and/or retinoids, can result in depigmentation, irritant dermatitis, and ochronosis (McDonald, C., *Prog. in Dermatol.* (1973) 4:15-20; Kligman, A., et al., *Arch. Dermatol.*, (1975) 111:40-48; and Hashaw, R., et al., *Arch. Dermatol.* (1985) 121:105-8.

The complications of acne are not limited to the skin of affected subjects. The physical symptoms of acne may contribute to the development of emotional and psychological distress, depression, anxiety and increased risks of suicide. (See, e.g., Kilkenny M, et al., *J Paediatr Child Health* (1997) 33:430-433; Smithard A, et al., *Br J Dermatol.* (2001) 145:274-279; Fried, R G, et al., *Dermatol Clin.* (2005) 23:657-664; and Purvis D, et al., *J Paediat Child Health*, (2006) 42:793-796.) The emotional distress which is caused by, or is otherwise aggravated by, the symptoms of acne may be particularly troublesome for adolescent subjects.

Various topical agents are utilized in the treatment of acne and these include sulfur, resorcinol, salicylic acid, benzoyl peroxide, retinoids and topical antibiotics. For example, commercially available topical treatments include both prescription and over-the-counter treatments, such as benzoyl peroxide to kill bacteria and dry the skin, salicylic acid to help unclog follicles, and sulfur. The topical use of retinoids to facilitate shedding of skin in an effort to help unclog follicles is also used to treat affected individuals.

Systemically available treatments have also been used to treat acne, including, for example tetracycline antibiotics such as minocycline. Generally, subjects are prescribed an extended course of antibiotic therapy and despite such extended therapies, the recurrence rate in these subjects is often high. Prescription antibiotics are also associated with a slow onset of action, which can lead to poor patient compliance.

Oral retinoids, such as isotretinoin, may also be effective; however their use is generally reserved for severe cases of acne due to the association of serious side effects, which may include teratogenicity, depression and suicidal ideation. Many of the available acne treatments are expensive and may cause considerable adverse effects. Furthermore, some medications may require continuous therapy and/or subjects may not promptly respond to such therapy or only achieve limited improvements during treatment.

Novel and effective therapies are needed for the treatment of acne, and in particular novel topical therapies that improve symptoms in a safe, rapid and effective manner are needed. There is also a need for treatments that are safe and that can be safely applied for extended periods of time and for treatments that quickly resolve the signs and symptoms of a dermatological disorder. Preferably, such therapies are stable and resistant to, for example, degradation following storage for extended periods of time.

SUMMARY OF THE INVENTION

The present inventions generally relate to pharmaceutical compositions, and in particular stable pharmaceutical compositions, as well as methods for treating subjects afflicted with or otherwise affected by one or more dermatological disorders (e.g., acne vulgaris and/or post-inflammatory hyperpigmentation (PIH)). The pharmaceutical compositions disclosed herein may be topically administered to a subject and are generally characterized by their ability to quickly (e.g., on the order of days) resolve the signs and symptoms of a dermatological disorder. Also disclosed herein are pharmaceutical compositions (e.g., topically administered compositions such as creams, ointments, serums, suspensions and/or solutions) that maintain a desired stability (e.g., remain stable at room temperature for at least two years or following exposure to freeze/thaw cycling).

In certain embodiments, the pharmaceutical compositions disclosed herein include one or more of arginine, salicylic acid and azelaic acid. Alternatively, in other embodiments the pharmaceutical compositions of the present invention include an arginine salt of salicylic acid (e.g., arginine salicylate) and/or an arginine salt of azelaic acid (e.g., arginine azelate). In still other embodiments, the pharmaceutical compositions of the present invention comprise the arginine, salicylic acid and azelaic acid in the form of a tripartite complex. For example, the compositions may include a tripartite complex or salt that comprises L-arginine bound (e.g., by one or more covalent or ionic interactions) to two or more acidic species, such as salicylic acid and/or azelaic acid.

In certain embodiments, the inclusion of arginine (e.g., L-arginine and alkyl esters thereof) in the topical pharmaceutical compositions facilitates (e.g., enhances or increases by at least about 2.5%, 5%, 10%, 25%, 30%, 50%, 75%, 90%, 100%, or more) the trans-epidermal absorption of one or more therapeutically effective agents (e.g., azelaic acid and salicylic acid). Such enhanced trans-epidermal absorption of the therapeutically effective agents may further enhance the efficacy of the pharmaceutical compositions disclosed herein. In some embodiments the compositions disclosed herein comprise chemically-modified arginine (e.g., ethyl esters of L-arginine). Contemplated modifications render the arginine more lipophilic and thereby optimize (e.g., increase) the ability of the arginine to permeate the stratum corneum layer of the skin and reach the underlying epidermis and dermis. Similarly, contemplated modifications of the arginine (e.g., alkyl esters of arginine) may further optimize (e.g., improve or otherwise enhance) the ability of one or more co-administered therapeutically effective agents (e.g., azelaic acid and/or salicylic acid) to permeate the stratum corneum layer of the skin and reach the underlying epidermis and dermis. In certain embodiments, the inclusion of, for example, an arginine alkyl ester in the pharmaceutical compositions disclosed herein may further enhance the efficacy of such pharmaceutical compositions. Accordingly, contemplated modifications to arginine include, for example, carboxylate alkyl esters of L-arginine (e.g., methyl and ethyl esters of L-arginine).

Certain aspects of the present invention relate to pharmaceutical compositions that are prepared as an emulsion (e.g., a stable emulsion). In some embodiments, such emulsions may include at least an aqueous phase and an oil phase. In certain embodiments, the emulsions disclosed herein also include a salt (e.g., an L-arginine salt of an acidic species such as salicylic acid, azelaic acid or hydrochloric acid). In certain embodiments, such salt may be dispersed, dissolved or suspended in the aqueous phase of the emulsion prior to combining the aqueous and oil phases. In other embodiments, such salt may be dispersed, dissolved or suspended in both the aqueous and oil phases of the emulsion prior to combining such aqueous and oil phases.

Also contemplated is the inclusion of one or more unsolubilized species in the emulsions disclosed herein, such as, for example unsolubilized azelaic acid. In certain embodiments, the unsolubilized species is micronized or is ultra-micronized. For example, in some embodiments the unsolubilized species comprises azelaic acid (e.g., free azelaic acid) having an average particle size of less than about 100 µm, 90 µm, 80 µm, 75 µm, 60 µm, 50 µm, 40 µm, 30 µm, 20 µm, 15 µm, 10 µm, 5 µm, 2.5 µm, 1 µm or smaller. In certain embodiments, the inclusion of such unsolubilized species into the emulsions disclosed herein will render the pharmaceutical composition more stable.

Preferably, the pharmaceutical compositions prepared in accordance with the teachings provided herein are stable. In one embodiment, the pharmaceutical compositions remain stable for at least about 30 days upon storage at about 50° C. In one embodiment, the pharmaceutical compositions remain stable for at least 60 days upon storage at 45° C. In one embodiment, the pharmaceutical compositions remain stable for at least 90 days upon storage at 40° C. In one embodiment, the pharmaceutical compositions remain stable for at least 2 years upon storage at 37° C. Preferably, the pharmaceutical compositions, and in particular the emulsions, disclosed herein are resistant to phase separation or "cracking". Similarly, in certain embodiments the pharmaceutical compositions (e.g., emulsions) disclosed herein are resistant to the development of precipitates. For example, when stored for extended periods (e.g., about one, two, three, six, twelve, eighteen, twenty-four, thirty-six months, or more at room temperature), upon visual inspection of the pharmaceutical compositions disclosed herein such compositions do not demonstrate phase separation or the development of a precipitate.

The pharmaceutical compositions of the present invention may be formulated or prepared to demonstrate favorable characteristics such as to render them particularly suitable for topical application. For example, the pharmaceutical compositions may be prepared to deliver one or more of azelaic acid, salicylic acid, L-arginine and/or a tripartite complex comprising all of the foregoing (e.g., a composition comprising azelaic acid bound to molecules of salicylic acid and L-arginine), in a pharmaceutically acceptable vehicle such as a lotion, cream, gel, ointment and/or serum. In some embodiments, the pharmaceutical compositions of the present invention are formulated as an oil, serum, ointment, cream, lotion, gel, shampoo, a saturated pad, spray or a cleanser. Such formulations may be packaged in convenient single-application or single-dose dispensers, or alternatively may be packaged in multi-application or multi-dose delivery packages. In certain embodiments, the pharmaceutical compositions of the present invention are prepared as a concentrated vehicle, such as a cream, ointment or serum.

One aspect of the present invention relates to pharmaceutical compositions comprising an arginine salt of salicylic acid. The arginine salt of salicylic acid may comprise at least about 0.25-25% by weight of the pharmaceutical composition (e.g., about 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20% w/w or more). Similarly, another aspect of the present invention relates to pharmaceutical compositions comprising an arginine salt of azelaic acid. In one embodiment, the arginine salt of azelaic acid comprises at least about 0.1-40% by weight of the composition (e.g., about 0.5%, 1%, 2.5%, 3%, 4%, 5%, 6%, 7%, 7.5%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30% w/w or more). In one embodiment, the arginine salt of azelaic acid comprises less than 15% by weight of the composition (e.g., about 0.25%, 0.5%, 1%, 2.5%, 3%, 4%, 5%, 6%, 7%, 7.5%, 8%, 9%, 10%, 11%, 12%, 13% or 14% w/w or more). Alternatively, another aspect of the present invention relates to pharmaceutical compositions comprising a tripartite complex of azelaic acid, salicylic acid and arginine. In one embodiment, the tripartite complex of azelaic acid, salicylic acid and arginine comprises at least about 2% by weight of the pharmaceutical composition (e.g., about 2.5%, 3%, 4%, 5%, 6%, 7%, 8%, 9%, 10%, 11%, 12%, 13%, 14%, 15%, 16%, 17%, 18%, 19%, 20%, 25%, 30% w/w or more).

In some embodiments, the pharmaceutical compositions disclosed herein further include additional ingredients, excipients or components (e.g., active and/or inactive ingredients). For example, the compositions disclosed herein may include additional pharmaceutical excipients such as, for example, emollients, skin conditioners, antioxidants, humectants, stabilizers, preservatives, fatty alcohols or emulsifiers, to improve the characteristics and the properties of the composition. In one embodiment, the pharmaceutical compositions of the present invention further include one or more antioxidants. For example, in one embodiment the pharmaceutical compositions include one or more antioxidants, such as lycopene. Such ingredients or components may further stabilize the pharmaceutical composition and/or may enhance the therapeutic effects of the pharmaceutical composition. For example, in some embodiments, the pharmaceutical compositions include one or more emulsifiers (e.g., polysorbate and/or polyacrylate crosspolymer-6). In other embodiments, the pharmaceutical compositions disclosed herein comprise one or more humectants or moisturizers (e.g., high and/or low molecular weight hyaluronic acids).

In some embodiments, the pharmaceutical compositions disclosed herein may comprise one or more anti-melanogenic compounds. Such anti-melanogenic compounds may be used to impart beneficial properties to the pharmaceutical compositions of the present invention, and may be particularly useful for the treatment of pigmentation dermatologic disorders (e.g., PIH, dark spots from aging or exposure to sunlight). Examples of suitable anti-melanogenic compounds may include, for example, one or more of glabridin, licorice or *glycyrrhiza glabra* root extract, hesperidin, kojic acid, kojic dipalmitate, azelaic acid, niacin, melanowhite and leukocyte extract.

The pharmaceutical compositions disclosed herein may further include one or more skin conditioners and/or humectants. For example, in one embodiment the pharmaceutical compositions include one or more skin conditioners selected from the group consisting of squalane, beta-glucan, hexylene glycol, butylene glycols, L-arginine and chamomile. In one embodiment the pharmaceutical compositions comprise one or more humectants selected from the group consisting of glycerin, hyaluronans and propylene glycol.

The pharmaceutical compositions of the present invention may further include one or more emollients, skin protectants and/or emulsifiers. For example, in one embodiment the pharmaceutical compositions include one or more emollients selected from the group consisting of isopropyl myristate, squalane, cyclopentasiloxane and dimethicone. In another embodiment the pharmaceutical compositions may also include willow bark as the skin protectant. In yet another embodiment the pharmaceutical compositions include polysorbate and/or polyacrylate crosspolymer-6 as the emulsifier.

In one embodiment, the pharmaceutical compositions of the present invention are prepared such that the arginine (e.g., as the arginine salt of azelaic acid and/or as the arginine salt of salicylic acid) is solubilized or partially-solubilized in the pharmaceutical composition (e.g., fully solubilized in the aqueous phase of an emulsion at room temperature).

Also disclosed are pharmaceutical compositions that are topically administered to a subject having or suspected of having one or more dermatological disorders. Dermatological disorders for which the pharmaceutical compositions disclosed herein may be used to treat include, for example, acne, PIH, rosacea, dyspigmentation, uneven skin tones and melasma. The pharmaceutical composition may be administered to the subject at least once daily, at least twice daily, at least three times daily, at least four times daily or more. In another embodiment, the pharmaceutical compositions of the present invention are administered to the subject topically in the evening or before bedtime. In still another embodiment, the pharmaceutical compositions of the present invention are administered in the morning.

The pharmaceutical compositions disclosed herein demonstrate favorable characteristics such as to render them particularly suitable for use in the treatment of several dermatological disorders. For example, upon application to a subject the pharmaceutical compositions disclosed herein are preferably capable of improving the signs and symptoms of acne (e.g., reduce excessive sebum production and/or reduce hyperpigmentation caused by acne scarring). Accordingly, one aspect of the present inventions relates to methods of treating one or more dermatological disorders, including, but not limited to acne and PIH. For example, in one embodiment the present invention relates to a method of treating a subject with a dermatological disorder by administering a pharmaceutical composition of the present invention to a subject (e.g., topically administering a composition comprising one or more agents selected from the group consisting of azelaic acid, salicylic acid and arginine). Also provided are methods of treating a dermatological disorder by topically administering a pharmaceutical composition comprising a tripartite complex of azelaic acid, salicylic acid and arginine to a subject. The dermatological disorders to be treated may include, for example, acne and/or PIH. In one embodiment of the present invention, the treated subject is an adolescent or an adult. In one embodiment of the present invention, the treated subject has dark pigmented skin or complexion, as classified, for example by the Fitzpatrick Classification Scale. For example, in some embodiments the treated subject may have Fitzpatrick Type I, Type II, Type III, Type IV, Type V or Type VI skin.

The pharmaceutical compositions and methods of the present invention preferably cure, resolve and/or improve the signs and/or symptoms of the dermatological disorder following administration to a subject. For example, in one embodiment of the present invention the signs and symptoms of the dermatological disorders (e.g., sebum production, the presence of acne lesions, inflammation, and/or scarring) improve or are otherwise resolved following the administration of the pharmaceutical compositions of the present invention over a shortened therapeutic course (e.g., about 3 days). In one embodiment of the present invention the signs and symptoms of the dermatological disorders (e.g., the presence of post-inflammatory hyperpigmentation) are improved, reduced, delayed or otherwise eliminated following the administration of the pharmaceutical compositions of the present invention for about 5 days, about 7 days, about one week, about two weeks, about three weeks, about four weeks, about six weeks, about eight weeks, about twelve weeks or more.

The above-discussed and many other features and attendant advantages of the present invention will become better understood by reference to the following detailed description of the invention when taken in conjunction with the accompanying examples. The various embodiments described herein are complimentary and can be combined or used together in a manner understood by the skilled person in view of the teachings contained herein.

BRIEF DESCRIPTION OF THE DRAWINGS

FIG. 1 is an illustration of a normal pilosebaceous unit (PSU). Found over most of the body, each PSU consists of a sebaceous gland connected to a canal, called a follicle that contains a fine hair.

DETAILED DESCRIPTION OF THE INVENTION

The present invention relates to novel pharmaceutical compositions and related methods of use for the treatment of dermatological disorders, which include, for example, acne vulgaris, acne rosacea and dermatological pigmentation disorders such as post-inflammatory hyperpigmentation (PIH) and melasma. Such pharmaceutical compositions are generally stable and comprise one or more arginine compounds in combination with a therapeutically-active compound such as salicylic acid and/or azelaic acid. The pharmaceutical compositions described herein are not plagued by the stability issues that typically characterize for example, other topically applied delivery vehicles. Rather, such pharmaceutical compositions are stable, and in certain instances are formulated as an emulsion. Such stable pharmaceutical compositions may demonstrate, for example, a reduced susceptibility to phase separation or "cracking" when stored for extensive periods of time.

In certain embodiments, the pharmaceutical compositions disclosed herein are formulated for the topical treatment of one or more dermatological disorders. While topically-applied therapies may be generally effective for the treatment of dermatological disorders, the efficacy of such therapies is often limited by the physical properties of the skin. The skin primarily serves as a barrier intended to limit the distribution of exogenous compositions into the underlying tissues (e.g., the dermis and epidermis). The barrier functionality of the skin is generally limited to the outermost layers of the skin known as the stratum corneum. While the barrier function of skin is protective in nature, it does present a challenge to the treatment of conditions that affect the skin, and in particular, presents specific challenges relating to the topical treatment of such conditions. For example, the barrier nature of the skin may limit the ability of a therapeutically-active agent to penetrate the stratum corneum of the skin and reach the underlying tissues (e.g., the dermis and epidermis) to thereby exert an intended beneficial effect.

In certain aspects, the pharmaceutical compositions disclosed herein have been prepared in an effort to enhance the distribution of one or more components (e.g., therapeutically-active agents such as azelaic acid) of such compositions into the tissues underlying the stratum corneum (e.g., the dermis and epidermis). For example, in certain embodiments, the pharmaceutical compositions of the present invention generally comprise arginine (e.g., L-arginine) in combination with one or more therapeutically-active agents. As used herein, the term "arginine" refers to the amino acid arginine (1-amino-4-guanidinovaleric acid), either in its base form or a pharmaceutically acceptable salt thereof (e.g., hydrochloride salts, malic acid salts, salicylic acid salts and/or azelaic acid salts of arginine). Unless otherwise provided, the term arginine also encompasses both the D- and L-enantiomers, as well as mixtures thereof, and also refers to esters, dimers, trimers and other polypeptide sequences of contiguous arginine residues (e.g., polypeptide chains or sequences comprising 2, 3, 4, 5, 6, 7, 8, 9, 10, 11, 12, 13, 14, 15, 16, 17, 18, 19, 20, 25, 30, 35, 40, 45, 50 or more contiguous arginine residues). The general structure of L-arginine is provided in Formula I.

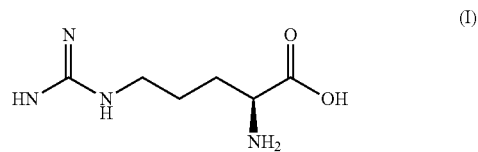 [SMILES: N=C(N)NCCC[C@H](N)C(=O)O]

Arginine plays an important role in cell division, the healing of wounds, removing ammonia from the body, immune function, and the release of hormones. Arginine, and in particular, L-arginine is also a substrate for the nitric oxide synthase enzymes (EC 1.14.13.39), which are capable of catalyzing the production of nitric oxide (NO). In certain aspects of the present inventions, the inclusion of one or more arginine compounds (e.g., L-arginine) in the pharmaceutical compositions of the present inventions facilitates (e.g., enhances or increases) the production of NO in the tissues of the skin (e.g., the dermis and epidermis) and thereby increases the permeability of the skin. Without wishing to be bound by any particular theory, it is believed that such increased permeability facilitates the absorption and/or distribution of other components of the pharmaceutical composition (e.g., therapeutically-active agents) into the skin of an affected subject (e.g., a subject with acne). In some embodiments, the inclusion of one or more arginine compounds in the pharmaceutical compositions of the present invention may increase the permeability of the skin by at least about 25% (e.g., about 40%, 50%, 75%, 100%, 200%, 250%, 300%, 400%, 500% or more) to thereby increase the distribution of, for example, one or more therapeutically-active agents into the skin.

While several embodiments of the present invention contemplate the inclusion of one or more arginine compounds as a component of the subject pharmaceutical compositions, it should be understood that such arginine compounds need not be limited to, for example, L-arginine. Also contemplated are arginine compounds into which one or more chemical modifications have been introduced. For example, contemplated are modifications made to L-arginine that are intended to render it more lipophilic or less polar, thereby enhancing the skin permeability of such L-arginine. Similarly, contemplated modifications to arginine may include modifications intended to neutralize an anionic species (e.g., the carboxylic acid group) of arginine. Suitable modifications may include esterification of the carboxylic acid group of arginine to form an alkyl ester of L-arginine. In certain embodiments, by esterifying the arginine the ability of arginine to form hydrogen bonds with the stratum corneum is reduced or otherwise nullified leaving the arginine alkyl ester to penetrate and carry with it one or more therapeutically-active agents below the stratum corneum (e.g., into the epidermis). In certain embodiments, modified L-arginine (e.g., carboxylate alkyl esters of L-arginine) retains the ability to act as substrates for nitric oxide synthase enzymes to thereby catalyze the production of nitric oxide (NO).

As used herein, the term "alkyl" refers to both straight and branched chain $C_1$-$C_{40}$ hydrocarbons (e.g., $C_6$-$C_{20}$ hydrocarbons), and include both saturated and unsaturated hydrocarbons. In certain embodiments, the alkyl may comprise one or more cyclic alkyls and/or one or more heteroatoms such as oxygen, nitrogen, or sulfur and may optionally be substituted with substituents (e.g., one or more of alkyl, halo, alkoxyl, hydroxy, amino, aryl, ether, ester or amide). The use of designations such as, for example, "$C_6$-$C_{20}$" is intended to refer to an alkyl (e.g., straight or branched chain and inclusive of alkenes and alkyls) having the recited range of carbon atoms. In certain embodiments, the alkyl group of the L-arginine alkyl ester is selected from the group consisting of ethyl, methyl, propyl, iso-propyl, butyl, iso-butyl, sec-butyl, ter-butyl, pentyl, hexyl, heptyl, octyl, nonyl and decyl.

In certain embodiments, the pharmaceutical compositions disclosed herein comprise an arginine compound (e.g., L-arginine) complexed, bound or otherwise associated with, for example, one or more therapeutically-active agents (e.g., salicylic acid and/or azelaic acid). By complexing, associating or otherwise binding one or more therapeutically-active agents with an arginine compound the transepithelial delivery and the therapeutic efficacy of such therapeutically-active agents may be modulated or enhanced (e.g., increased by at least about 2.5%, 5%, 7.5%, 10%, 12.5%, 15%, 20%, 25%, 30%, 40%, 50%, 60%, 70%, 75%, 80%, 90%, 100%, 150%, 200%, 250%, 300%, 400%, 500% or more). For example, in certain aspects, the association of an arginine compound with one or more therapeutically-active agents (e.g., azelaic acid) facilitates the penetration and/or absorption of such therapeutically-active agents into the stratum corneum, thereby enhancing the distribution of such therapeutically-active agents into the underlying tissues of the skin (e.g., the dermis and epidermis).

Accordingly, one embodiment of the present invention relates to the binding of an arginine species to one or more therapeutically-active agents. As used herein in the context of binding arginine to one or more therapeutically-active agents, the terms "bound" and "binding" refer to any form of chemical linkage or association such as from hydrogen bonding, covalent bonds, non-covalent associations, ionic interactions, electrostatic interactions, hydrophobic interactions, and the like. Contemplated covalent bonds include, but are not limited to, ester, ether, amide and carbamide bonds. Contemplated electrostatic interactions include for example, ionic bonds, hydrogen bonds, salt bridges and van der Waals interactions. The pharmaceutical compositions of the present invention may comprise one or more arginine (e.g., L-arginine) residues or species bound to one or more therapeutically-active agents, such as a therapeutically-active organic compound (e.g., azelaic acid and/or salicylic acid). In one embodiment of the present invention the arginine compound or species (e.g., a dimer or trimer of L-arginine) is bound (e.g., covalently bound) to one or more therapeutically-active organic compounds (e.g., salicylic acid and/or azelaic acid). In one embodiment, the arginine species of the present invention may bind to the therapeutically-active organic compounds through one or more of the amino group, carboxy group or guanidino group of arginine. In those certain embodiments where the therapeutically-active organic compound is an acidic species (e.g., salicylic acid and/or azelaic acid), such therapeutically-active compound may bind, conjugate, complex or otherwise interact with the positively guanidinium ($CH_6N_3^+$) group or species of arginine (e.g., L-arginine). In another embodiment, the complex may comprise one or more of the arginine compounds bound (e.g., by one or more ionic interactions) to two or more therapeutically-active organic compounds.

The ability of arginine to form multiple bonds (e.g., hydrogen bonds) makes it particularly suitable for binding negatively charged groups or species (e.g., acidic species such as salicylic acid, azelaic acid or hydrochloric acid). Accordingly, in one embodiment the pharmaceutical compositions of the present invention comprise one or more arginine species or residues bound to one or more therapeutically-active species, such as azelaic acid and salicylic acid, to form an aggregate or complex. For example, in one embodiment the pharmaceutical compositions of the present invention comprise one or more arginine species bound (e.g., by hydrogen bonds) to one or more azelaic acid species, as depicted below:

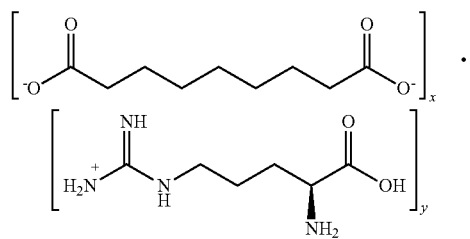

wherein "x" and "y" are each any positive integer (e.g., "x" and "y" are independently selected from the group consisting of one, two, three, four, five, six, seven, eight, nine, ten, eleven, twelve, thirteen, fourteen, fifteen, sixteen, seventeen, eighteen, nineteen, twenty, or more). In one embodiment, each of "x" and "y" is one. In another embodiment, "x" is one and "y" is two. Alternatively, in certain other embodiments, "x" is two and "y" is one.

The pharmaceutical compositions of the present invention may comprise one or more arginine species bound (e.g., by hydrogen bonds) to one or more salicylic acids species, as depicted below:

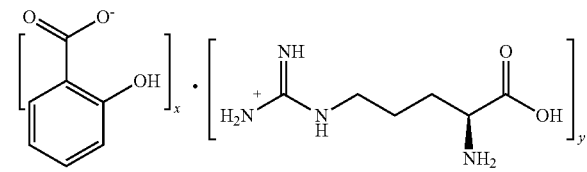

wherein "x" and "y" are each any positive integer (e.g., "x" and "y" are independently selected from the group consisting of one, two, three, four, five, six, seven, eight, nine, ten, eleven, twelve, thirteen, fourteen, fifteen, sixteen, seventeen, eighteen, nineteen, twenty, or more). For example, in certain embodiments each of "x" and "y" is one. Alternatively, in certain other embodiments, "x" is two and "y" is one. In still another embodiment, "x" is two and "y" is one.

The term "complex" is used herein to refer to the association or aggregation of a plurality of species (e.g., arginine and one or more therapeutically-active agents). For example, contemplated by the present invention are both the covalent binding and/or non-covalent associations (e.g., van der Waals interactions) of arginine, azelaic acid and salicylic acid with one another to form an aggregate or complex. For example, in one embodiment the pharmaceutical compositions of the present invention comprise one or more arginine species bound (e.g., by hydrogen bonds or salt bridges) to one or more azelaic acid species and one or more salicylic acid species, as depicted below:

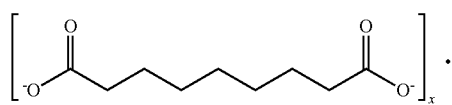

-continued

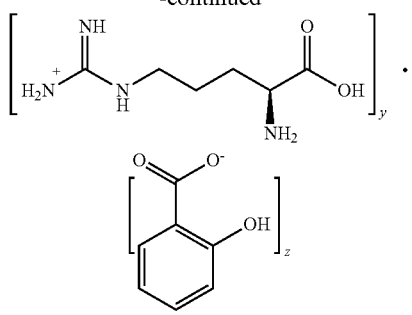

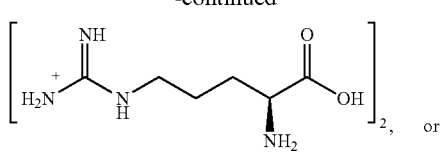

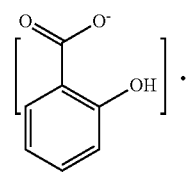

wherein "x", "y" and "z" are each any positive integer (e.g., "x", "y" and "z" are independently selected from the group consisting of one, two, three, four, five, six, seven, eight, nine, ten, eleven, twelve, thirteen, fourteen, fifteen, sixteen, seventeen, eighteen, nineteen, twenty, or more). In certain embodiments, "x" equals 1, "y" equals 2 and "z" equals 1. In other embodiments, "x" equals 1, "y" equals 4 and "z" equals 2. In still other embodiments, "x" equals 2, "y" equals 5 and "z" equals 1. In certain embodiments the sum of "x", "y" and "z" is equals three or more (e.g., each of "x", "y" and "z" equals one or alternatively "y" equals two and either "x" or "z" equals one). For example, in one embodiment, "x", "y" and "z" are each one, thereby forming a tripartite complex as depicted below:

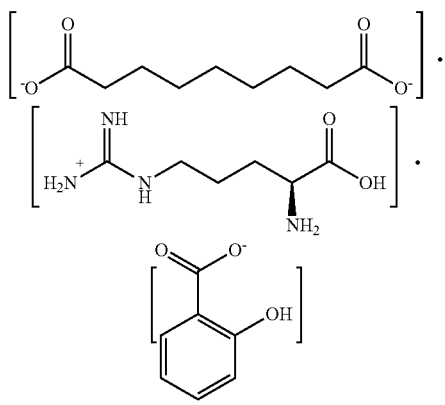

As used herein to describe a complex, the term "tripartite" refers to a molecular complex composed of or comprising three or more parts or species (e.g., where each of "x", "y" and "z" equals one). For example, disclosed herein is a tripartite complex comprising two or more therapeutically-active agents (e.g., azelaic acid and/or salicylic acid) capable of forming a complex (e.g., a salt) with arginine (e.g., L-arginine or an alkyl ester thereof). In other embodiments, the tripartite complex comprises two or more arginine compounds (e.g., L-arginine and alkyl esters thereof) complexed with one or more therapeutically-active agents, for example as depicted below:

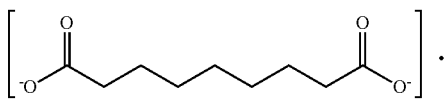

In certain other embodiments, the individual components or species of such tripartite complex are bound (e.g., covalently or non-covalently) to each other (e.g., by one or more ionic interactions).

In certain embodiments, the tripartite complex comprises L-arginine, salicylic acid and azelaic acid. For example, the tripartite complex may comprise two L-arginine species, one salicylic acids species and one azelaic acid species, as represented by the structure below:

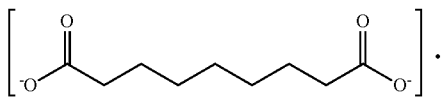

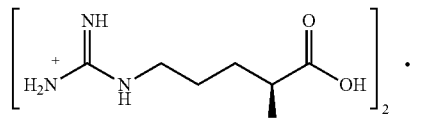

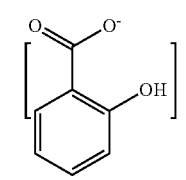

Similarly, the tripartite complex disclosed herein may comprise three L-arginine species, two salicylic acids species and one azelaic acid species, as represented by the structure below:

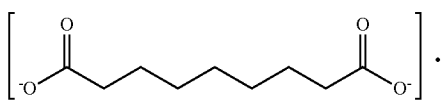

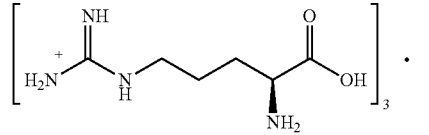

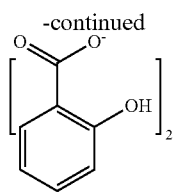

In certain embodiments, the tripartite complex has a net neutral charge. In other embodiments, the tripartite complex has an overall negative charge (e.g., about −1, −2, −3 or −4). In still other embodiments, the tripartite complex has an overall positive charge (e.g., about +1, +2, +3 or +4).

The complexes described herein (e.g., tripartite complexes comprising L-arginine, azelaic acid and salicylic acid) preferably retain the therapeutic activity or efficacy of each constituent species. For example, in certain embodiments, the tripartite complex dissociates or otherwise releases the constituent species following administration to a subject, thereby allowing such constituent species to exert their intended therapeutic effect. In certain aspects, the complexes (e.g., a complex comprising L-arginine and one or more of azelaic acid and salicylic acid) may demonstrate a synergistic therapeutic efficacy relative to the constituent species which comprise the complex (e.g., therapeutic efficacy may be improved by about one-, two-, three-, four-, five-, six-, seven-, eight-, nine-, ten-, twelve-, fifteen-, twenty-fold, or more relative to the individual components). Accordingly, in certain embodiments, the therapeutic efficacy or activity of the complex is synergistically enhanced relative to the therapeutic efficacy or activity of the individual components of the complex, such that the efficacy of the complex is more than the sum of the efficacy of each of the constituent species when evaluated in isolation. For example, contemplated are pharmaceutical compositions that comprise both salicylic acid and azelaic acid (e.g., a tripartite complex comprising salicylic acid, azelaic acid and L-arginine) present in concentrations such that they act in synergy to confer therapeutic activity or efficacy on the pharmaceutical compositions which is greater than the sum of the therapeutic activity which is observed, or would otherwise be expected, following the administration of each of the salicylic acid and azelaic acid separately.

In certain embodiments, the synergistic therapeutic efficacy observed with the pharmaceutical compositions of the present invention may be exploited to effectuate a corresponding reduction in the amount of one or more therapeutically-active agents necessary to achieve one or more clinical endpoints (e.g., resolution of acne symptoms or reduced pigmentation). In one embodiment, the synergy demonstrated by the pharmaceutical compositions of the present invention enable a lower dose of each constituent therapeutically-active agent contained therein to be administered to the subject, thereby reducing the incidence of adverse reactions. For example, when formulated in a pharmaceutical composition comprising salicylic acid and arginine (e.g., a pharmaceutical composition comprising L-arginate salts of one or more of salicylic acid and azelaic acid) lower doses of azelaic acid (e.g., less than 15% w/w, less than 14% w/w, less than 12.5% w/w, less than 10% w/w, less than 7.5% w/w, less than 6% w/w, less than 5% w/w, less than 4% w/w, less than 3% w/w, less than 2.5% w/w, less than 2% w/w, less than 1% w/w, less than 0.5% w/w or less than 0.25% w/w) may demonstrate therapeutic efficacy generally equivalent with that observed following the administration of a topical formulation comprising about 15-20% w/w of azelaic acid.

The pharmaceutical compositions disclosed herein generally comprise at least one therapeutically-active agent. As used herein, the phrases "therapeutically-active" and "therapeutic activity" as they qualify an agent or species refer to the ability of such an agent or species to treat or cure a disease or condition, or to treat, cure or otherwise mitigate the subjective and/or objective signs and symptoms of a disease or condition, and in particular a dermatological disorder. As will be appreciated by those of skill in the art, the therapeutic activity of a compound may be measured or monitored using objective and/or subjective means. In some embodiments of the invention, therapeutic activity relates to the ability of one or more therapeutic compounds or agents to improve the objective signs and symptoms of acne (e.g., a statistically significant reduction in mean inflammatory lesion count, erythema severity, pigmentation, acne scarring and/or sebum production). In other embodiments of the present invention, therapeutic activity relates to a subject's subjective perception regarding their dermatological disorder. Contemplated therapeutically-active agents or species that may be used in accordance with the present invention include any compounds or drugs that may be used to treat a disease or condition (e.g., a dermatological disorder). Such therapeutically-active compounds may include, for example, benzoyl peroxide, salicylic acid, azelaic acid, urea, tretinoin, sulfur, resorcinol, erythromycin, clindamycin, tetracycline, minocycline, mixtures of the foregoing or any other suitable therapeutically-active compounds disclosed in standard reference texts, such as the British and United States Pharmacopoeias, Remington's Pharmaceutical Sciences (Mack Publishing Co.) and Martindale The Extra Pharmacopoeias (London, The Pharmaceutical Press), the disclosures of which are incorporated herein by reference in their entirety.

In certain embodiments, the pharmaceutical compositions disclosed herein comprise two or more therapeutically-active agents (e.g., azelaic acid and salicylic acid). In instances where the pharmaceutical compositions disclosed herein comprise two or more therapeutically-active agents, such therapeutically-active agents may exert a therapeutic benefit using different mechanisms of action.

In one embodiment, the therapeutically-active agent comprises one or more dicarboxylic acid compounds, such as azelaic acid. Azelaic acid, or 1,7-heptanedicarboxylic acid, is a naturally occurring straight-chained, 9-carbon atom saturated dicarboxylic acid obtained by oxidation of oleic acid and by chemical, physical or biological oxidation of free and esterified fatty acids. Azelaic acid is known for its anti-bacterial and comedolytic properties and has been used clinically for the treatment of acne and hyperpigmentation disorders. (Fitton, A., et al., *Drugs* (1991) 41 (5):180-798.) Generally, azelaic acid is an effective and well-tolerated monotherapy in mild and moderate forms of acne and is comparable in its efficacy to other topical acne treatments, such as benzoyl peroxide. (Liu, R., et al., *Arch. Dermatol.* (2006) 142(8): 1047-1052.) Azelaic acid also inhibits the growth of *P. acnes*, and normalizes the disturbed follicular keratinization process and in addition may demonstrate anti-inflammatory properties.

Because dicarboxylic acids such as azelaic are characterized by having two distinct carboxyl groups, they can form two kinds of salts and/or esters, (e.g., with L-arginine). Accordingly, in one embodiment the pharmaceutical compositions of the present invention comprise an arginine salt of azelaic acid (e.g., both mono- and di-arginine salts of azelaic acid). Other dicarboxylic acids contemplated by the present invention include, for example, adipic acid, pimelic acid, suberic acid, sebacic acid, undecanedioic acid, dodecanedioic acid, and combinations and salts and/or esters thereof. In one embodiment, the compositions of the present comprise an effective amount of azelaic acid. For example, in one embodiment, the concentration of azelaic acid in the present invention is less than 20% w/w, less than 15% w/w, less than 12.5% w/w, less than 10% w/w, less than 7.5% w/w, less than 6% w/w, less than 5% w/w, less than 4% w/w, less than 3% w/w, less than 2.5% w/w, less than 2% w/w, less than 1% w/w or less than 0.5% w/w.

In certain embodiments, the therapeutically-active agent comprises salicylic acid or a salt and/or ester thereof (e.g., L-arginine salicylate). When applied topically to the skin salicylic acid promotes the sloughing off of dead skin cells, thereby preventing or slowing the clogging of pores. In one embodiment, the pharmaceutical compositions of the present invention comprise salicylic acid. In another embodiment, the salicylic acid is present as an arginine salt (i.e., arginine salicylate). The concentration of the salicylic acid (e.g., arginine salicylate) in the pharmaceutical composition may be at least about 0.05% w/w, at least about 0.1% w/w, at least about 0.25% w/w, at least about 0.5% w/w, at least about 1% w/w, around about 2% w/w, at least about 2.5% w/w, at least about 3% w/w, at least about 3.5%, w/w at least about 5% w/w, at least about 7.5% w/w or at least about 10% w/w.

The pharmaceutical compositions of the present invention are particularly suitable for the treatment of one or more dermatological disorders. As used herein, the phrase "dermatological disorder" refers to any disease or condition of the skin, dermis, or any substructure therein. Dermatological disorders include, for example, acne vulgaris, pigmentation disorders such as post-inflammatory hyperpigmentation, dyspigmentation, melasma, uneven skin tone, or hyperpigmentation or dark spots resulting from aging or exposure to sunlight or ultraviolet radiation, acne rosacea, xeroderma, psoriasis, ectopic dermatitis, skin cancers, and any other disease or condition affecting the skin, dermis or structures therein. In certain embodiments, the hyperpigmentation disorder is one or more selected from the group consisting of hyperpigmentation (e.g., PIH), dyspigmentation, dark spots resulting from aging or exposure to sunlight or ultraviolet radiation, uneven skin tone and/or melasma. The compositions disclosed herein may also be useful for the treatment of pre-malignant skin conditions (e.g., lentigo maligno and melanoma). For example, in embodiments where the pharmaceutical compositions comprise azelaic acid, the azelaic acid may impart anti-tumoral properties to the compositions. (See, e.g., Breathnach, *Cutis* (1996); 57(1 Suppl): 36-45; Del Rosso, *Cutis* (2006); 77(2 Suppl): 22-4; and Leibl, et al. *Invest Dermatol* (1985); 85(5):417-22, the contents of which are incorporated herein by reference in their entirety.) The pharmaceutical compositions of the present invention are particularly suitable for treating dermatological disorders by topically administering such compositions to a subject affected by such dermatological disorder.

In certain embodiments, the dermatological disorder is acne vulgaris. Acne vulgaris is a dermatological disorder resulting from the action of hormones and other substances on a subject's sebaceous glands and hair follicles, which result in plugged pores and outbreaks of lesions commonly referred to as pimples. Acne is frequently referred to as a disease of the pilosebaceous units (PSU), which are found over most of the body. As depicted in FIG. 1, each PSU consists of a sebaceous gland connected to a canal, called a follicle that contains a fine hair. Although acne is generally not viewed as a serious health threat, it can be a source of significant emotional distress and in some severely affected subjects can lead to permanent scarring of the skin.

Subjects affected by acne frequently present with a variety of topical lesions. The basic acne lesion, called the comedone, is simply an enlarged and plugged hair follicle. If the plugged follicle, or comedone, stays beneath the skin, it is referred to as a closed comedone and produces a white bump referred to as a whitehead. A comedone that reaches the surface of the skin and opens up is referred to as an open comedone or blackhead because it looks black on the skin's surface.

The pharmaceutical compositions of the present invention are useful for the treatment of dermatological disorders and accordingly, one embodiment of the present invention relates to methods of treating a dermatological disorder by administering an effective amount of one or more of the pharmaceutical compositions of the present invention (e.g., a pharmaceutical composition comprising arginine salicylate) to a subject, and in particular, a subject having a dermatological disease. As used herein, the term "subject" means any mammal, including humans. In certain embodiments of the present invention the subject is an adult or an adolescent. In one embodiment of the present invention, the subject has dark pigmented skin or complexion, as classified, for example by the Fitzpatrick Classification Scale (e.g., Fitzpatrick Type I, Type II, Type III, Type IV, Type V or Type VI skin). See, Fitzpatrick. *J Med Esthet.* (1975) 2:33034.

The contemplated methods may comprise, for example, the treatment of a dermatological disorder by administering an effective amount of a pharmaceutical composition comprising a tripartite complex of azelaic acid, salicylic acid and L-arginine to a subject at least once daily (e.g., at bedtime), at least twice daily (e.g., in the morning and in the evening), at least three times daily, at least four times daily or more. Upon administering an effective amount of the pharmaceutical compositions of the invention to a subject, such compositions are preferably capable of improving the signs and symptoms of the dermatological disorder (e.g., reduce excessive sebum production and/or reduce hyperpigmentation caused by acne scarring). In another embodiment, the present invention relates to the treatment of a subject with, for example, acne by topically administering on a regular basis (e.g., once daily) a topical pharmaceutical composition to the affected area of the subject, wherein the pharmaceutical composition comprises, for example, the arginine salts of azelaic acid and/or salicylic acid.

Several factors may be considered to determine the effective amount or the dosing frequency, dosing interval and/or treatment duration with which the pharmaceutical compositions of the present invention may be administered to a subject and such factors may vary based on the condition of the subject and/or the severity of the dermatological disorder. As used herein, the term "effective amount" means an amount sufficient to achieve a meaningful benefit to the subject (e.g., treating, modulating, curing, preventing and/or ameliorating the underlying dermatological disorder). An effective amount of the pharmaceutical compositions of the present invention may be generally determined based on an amount sufficient to achieve a desired therapeutic effect. Generally, the amount of the pharmaceutical composition administered to a subject in need thereof will depend upon the characteristics of the subject and the severity of the dermatological disorder. Such characteristics may include for example, the condition, general health, age, subjective symptoms, objective appearance, sex and body weight of the subject. One of ordinary skill in the art will be readily able to determine an effective amount depending on these and other related factors. Additionally, both objective and subjective assays may be optionally employed by one of ordinary skill in the art to further identify optimal dosage ranges. Preferably, a therapeutically effective amount is sufficient to significantly and positively modify the condition to be treated (e.g., acne) while minimizing or avoiding serious adverse effects.

The compositions of the present invention are also characterized by the speed with which subjects achieve relief of their dermatological disorder. For example, in one embodiment, the pharmaceutical compositions of the invention are capable of improving the signs and symptoms of a dermatological disorders within about three, five, seven, ten, fourteen, twenty or thirty days. In another embodiment, upon applying the pharmaceutical compositions of the invention, a subject is able to notice improvement within about five days, about seven days, about ten days, about two weeks, about four weeks, about six weeks, about eight weeks, about ten weeks, or about twelve weeks of use.

The therapeutically-active agents that comprise the pharmaceutical compositions may be delivered topically using one or more pharmaceutically-acceptable carriers or vehicles. Preferably, the pharmaceutical compositions disclosed herein can be applied directly to the skin of a subject. In certain embodiments, the vehicles or carriers that comprise the pharmaceutical compositions comprise, consist of or are otherwise prepared as an emulsion. In other embodiments, such pharmaceutical compositions are stable and/or remain stable following their preparation. The pharmaceutical compositions of the invention may be formulated in any form suitable for application to the site of interest, and include, for example, an oil, serum, ointment, cream, lotion, gel, shampoo, a saturated pad, spray, cleanser, or the like.

As used herein to characterize a pharmaceutical composition, the term "stable" refers to the physical stability of such compositions and generally means that the compositions are suitable for administration to a subject at the conclusion of a predetermined period of time and/or storage conditions (e.g., following storage at standard room temperature and humidity for at least two years). In certain embodiments the substantial absence of a precipitate, cloudiness and/or other particulate matter (e.g., following storage at 45° C. for at least two months) in the composition may be indicative of its stability. In other embodiments (e.g., where the pharmaceutical composition is formulated as an emulsion), the substantial absence of a phase separation or "cracking" (e.g., following storage at 50° C. for at least one month) may be indicative of the stability of the pharmaceutical compositions disclosed herein.

In other embodiments, the pharmaceutical compositions disclosed herein (e.g., emulsions comprising a tripartite complex comprising azelaic acid, salicylic acid and L-arginine) are stable (e.g., at about 33.5° C.) following exposure to freeze/thaw cycling. For example in some embodiments, the pharmaceutical compositions disclosed herein are stable at room temperature (e.g., as evident by the lack of appreciable phase separation) following exposure to one, two, three, four or more freeze/thaw cycles (e.g., a cycle comprising freezing the composition for about twenty-four hours at about −5° C., followed by thawing at 40° C.).

Proceeding contrary to accepted wisdom, the present inventors have prepared pharmaceutical compositions, and particularly emulsions, that have demonstrated stability for extended periods (e.g., following storage at 40° C. for at least three months).

The term "emulsion" is used generally herein to refer to a composition comprising a continuous aqueous phase with an oil phase dispersed as discrete droplets or particles therein. The aqueous phase may comprise water or other water soluble substances, and include, for example water-soluble polymers, or any combination thereof (e.g., alcohols, glycols and glycerin). In certain embodiments, the oil phase comprises about 0.01% to 40% of the pharmaceutical composition (e.g., about 5-20%). The oil phase may generally comprise one or more oils or oil-soluble substances (e.g., emollients, fatty alcohols, skin conditioners and antioxidants). In certain embodiments, the emulsions comprise one or more salts (e.g., L-arginine azelate or a tripartite complex comprising L-arginine azelate) solubilized in the aqueous phase. Generally, such pharmaceutical compositions may be prepared by combining an aqueous phase and an oil phase in accordance with methods routinely known to one of skill the art. In certain embodiments, the emulsions comprise a salt (e.g., one or more salts selected from the group consisting of L-arginine azelate, L-arginine salicylate, L-arginine HCL) dispersed in one or more of the oil phase and/or the aqueous phase of the emulsion. The present inventors have surprisingly determined that the inclusion of one or more salts in the emulsions (e.g., an arginine salt solubilized in the aqueous phase) may contribute to the stability of the pharmaceutical compositions disclosed herein.

One or more of the therapeutically-active agents of the present invention may be either solubilized or partially-solubilized in the pharmaceutical composition or carrier such that the therapeutically-active agents will not exist to any appreciable degree in a particulate or crystalline form in the pharmaceutical composition. For example, a therapeutically-active agent may be included in the pharmaceutical composition as a salt (e.g., a salt of L-arginine) and solubilized in one or more of the aqueous or oil phases of an emulsion. In certain embodiments, it may be preferable to maintain one or more of the therapeutically-active agents of the present invention in an unsolubilized or particulate form. The inclusion of one or more particulate therapeutically-active agents in the pharmaceutical compositions may serve to further stabilize such composition. For example, particulate azelaic acid (e.g., in its base form) may be included or otherwise dispersed into an emulsion to cause the adsorption of such particulate azelaic acid onto the discrete droplets or particles that comprise one or both of the the oil and/or aqueous phases of the emulsion. Without wishing to be bound by any particular theory, it is believed that the adherence of such particulate therapeutically-active agents may further stabilize the emulsion by preventing the oil and/or aqueous phases of the emulsion from coalescing. Accordingly, in embodiments where the pharmaceutical compositions comprise or consist of an emulsion, such emulsions may include one or more particulate or unsolubilized therapeutically-active agents. In certain embodiments, such unsolubilized therapeutically-active agents are micronized (e.g., by milling or other suitable particle reduction methods), such that the mean particle size of such therapeutically-active agent in the composition is less than about 1,000 µm, 900 µm, 800 µm, 750 µm, 600 µm, 500 µm, 400 µm, 300 µm, 250 µm, 200 µm, 100 µm, 90 µm, 80 µm, 75 µm, 60 µm, 50 µm, 40 µm, 30 µm, 20 µm, 15 µm, 10 µm, 5 µm, 2.5 µm, 1 µm or smaller. In certain embodiments, the micronized therapeutically-active agents demonstrate an enhanced ability to penetrate the stratum corneum.

In certain embodiments, the pharmaceutical compositions disclosed herein may also comprise one or more additional excipients that may impart one or more beneficial properties to the composition (e.g., improve stability, physical appearance or enhance therapeutic efficacy). For example, in certain embodiments, the topical pharmaceutical compositions disclosed herein may comprise one or more antioxidants (e.g., lycopene). In some embodiments, the pharmaceutical compositions disclosed herein may also comprise one or more antibacterial agents (e.g., azelaic acid, benzoyl peroxide and/or tea tree oil).

Similarly, in certain embodiments the compositions presented herein may comprise components such as one or more anti-melanogenic compounds (e.g., glabridin) to improve the appearance of hyperpigmented regions of the skin. Such anti-melanogenic compounds may be particularly useful for the treatment of dermatological or pigmentation disorders (e.g., PIH, dark spots from aging or exposure to sunlight). Examples of suitable anti-melanogenic compounds include, for example, one or more of glabridin, licorice root extract or *glycyrrhiza glabra* root extract, hesperidin, retinoic acid derivatives, hydroquinone, kojic acid, kojic dipalmitate and azelaic acid. Where the pharmaceutical compositions described herein comprise glabridin, such glabridin may be included in the form of a 40% solution and at a concentration of up to about 0.05%-5% w/w of the composition. Alternatively, in other embodiments, glabridin may be included in the pharmaceutical composition in the form of licorice root or *glycyrrhiza glabra* root extract. Such excipients or ingredients may be formulated or otherwise incorporated into the compositions of the present invention, for example, by dispersing, suspending or solubilizing such excipients or ingredients in one or more of an aqueous phase or an oil phase that comprises an emulsion.

In other embodiments, the pharmaceutical compositions may include one or more humectants. Generally, such humectants may include one or more of glycerin, high and low molecular weight hyaluronic acid and propylene glycol. In certain embodiments, the selected humectants may comprise between about 0.5-30% w/w of the composition. In certain embodiments, the pharmaceutical compositions disclosed herein may also include one or more skin conditioners (e.g., one or more skin conditioners selected from the group consisting of squalane, beta-glucan, hexylene glycol, butylene glycols, L-arginine and chamomile). The pharmaceutical composition of the present invention may further comprise one or more emollients or other excipients or compounds capable of hydrating the skin of a subject (e.g., isopropyl myristate, squalane, cyclopentasiloxane and/or dimethicone), as well as one or more skin protectants (e.g., willow bark). In other embodiments, the pharmaceutical compositions disclosed herein comprise one or more moisturizers (e.g., L-arginine, high and/or low molecular weight hyaluronic acids or hyaluronans).

While certain compounds, compositions and methods of the present invention have been described with specificity in accordance with certain embodiments, the following examples serve only to illustrate the compounds of the invention and are not intended to limit the same. The articles "a" and "an" as used herein in the specification and in the claims, unless clearly indicated to the contrary, should be understood to include the plural referents. As used herein, the term "about" will be understood by persons of ordinary skill in the art and may vary to some extent on the context in which such term is used. To the extent that there may be uses of the term which are not immediately clear to persons of ordinary skill in the art given the context in which is used, the term "about" will mean up to plus or minus twenty percent of the given term. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXAMPLES

Example 1

The present example relates to the preparation of a pharmaceutical composition in the form of a serum and that is useful for the treatment of, for example, acne.

The serum was prepared by adding approximately 49.477 g of ethoxydiglycol (TRANCUTOL CG) and 20.0 g of propanediol (ZEMEA) to a 200 ml beaker, followed by heating at 60° C. With moderate agitation, 2.0 g of salicylic acid and 14.0 g of azelaic acid (ORISTAR AZA) were then added to the beaker with continued agitation until completely dissolved. With moderate agitation, 2.0 g of L-arginine (ORISTAR LAG) was then added to the beaker with continued agitation until completely dissolved, followed by cooling of the formulation to 45° C. Approximately 7.317 g of specially denatured alcohol 40B, 5 g of Melaleuca Alternifolia (Tea Tree) Leaf Oil, 0.1 g of NAB willow bark extract, 0.1 g of Actiphyte of Chamomile BG50P (20.0%), and 0.006 g of lycopene (ORISTAR LP) were then added to a 20 ml beaker and homogenized to dissolve the lycopene. The contents of the 20 ml beaker were then added to the 200 ml beaker and the resulting pharmaceutical composition cooled to room temperature.

Approximately 100 g of acne serum was produced comprising a tripartite complex of azelaic acid, salicylic acid and arginine. Following exposure to freeze/thaw cycling at −5° C., the serum was stable at 25° C. for 6 months. It was noted that at 40° C., 45° C. and 50° C., the formation of a precipitate was evident within 2 months.

Example 2

The present example relates to the preparation of a pharmaceutical composition in the form of a stable emulsion that is useful for the treatment of dermatological disorders.

The oil phase of the emulsion was prepared in a 50 ml beaker by adding 3.0 g of cetyl alcohol C16-98, NF (Univar), 3.0 g of Stearyl Alcohol C18-98, NF (Univar), 9.8 g of Isopropyl Myristate NF (Inolex), 2.0 g of Squalane (Arista), 2.0 g of Kojic Acid Dipalmitate (Caribbean Natural Products), 2.4 g of SepiMax Zen (Seppic), 1.0 g of Tego SAS 60 (Evonik) and 4.0 g of Promulgin D (Lubrizol) mixed and heated to 70-75° C.

The aqueous phase of the emulsion was prepared in a 250 ml beaker by adding 112.4796 g of deionized water and with moderate mixing by vortex, slowly sifting 1.3 g of Avicel PC 611 (FMC) Deveraux into the deionized water, which was then followed by homogenization for 10 minutes at 10,000 rpm (32 mm rotor). The resulting phase was then heated to 70-75° C. and 10 g of glycerin 99.7% (Univar) was added, followed by the addition of the oil phase from the first kettle at 55° C. with moderate mixing.

With continued mixing, 4.0 g of salicylic acid USP (Rhodia), 2.0 g of L-Arginine Ethyl Ester (Pure Bulk), and 8.0 g of L-Arginine (OriStar LAG) were individually and sequentially added to the combined mixture. The mixture was then cooled to below 45° C. and 4.0 g of Cosmetic Fluid 8805 (Chemtec), 2.0 g of Euxyl PE 9010 (Schuke & Mayr), 0.2 g of Anthemus Nobilis (Chamomile) Extract (ACTIVE Organics), 0.2 g of *Glycyrrhiza Glabra* Root Extract (Formulex of Licorice Root VTF-0052.111), 0.2 g of Salix Nigra (Willow) Bark Extract, 0.2 g of Hyaluronate mixture and 0.02 g of beta-Glucan (OriStar BG) were individually and sequentially added to the mixture.

A mixture was prepared by combining 0.2 g of isopropyl myristate NF (Inolex), and 0.0002 g of lycopene (OriStract LP), BioAstin SCE 5 (Cyanotech) Astaxanthin was added to the emulsion and mixed under vacuum to deaeroate the batch.

Finally, 28 g of azelaic acid (Cognis) was sifted into a vortex and mixed under vacuum for 30 minutes followed by homogenization for 5 minutes at 5,000 rpm (32 mm Rotor). The resulting cream was stable at all conditions tested for at least 2.5 months and had a concentration of 14% azelaic acid, 2% salicylic acid, a pH of approximately 4.8-5.2, viscosity (LVT #4 at 3 RPM) of 700,000 cSt, and spg of 0.995.

Example 3

The present example relates to the preparation of a pharmaceutical composition in the form of an emulsion and that is useful for the treatment of dermatological disorders. An aqueous phase was prepared with moderate mixing in a 250 ml beaker by adding 79.69 g of deionized water, 10.0 g of glycerin 99.7% (Univar) and 6.0 g of Transcutol CG (Gattefosse), followed by the individual and sequential addition of 4.0 g of salicylic acid USP (Rhodia), 8.0 g of L-Arginine (OriStar LAG) and 2.0 g of L-Arginine Ethyl Ester (Pure Bulk) and until completely dissolved. With moderate mixing, 28.0 g of azelaic acid (Cognis) was then slowly sifted into the mixture. The resulting mixture was deaerated with vacuum, followed by the addition of 1.0 g of SepiMax Zen (Seppic) and additional mixing for 20 minutes.

To a second 100 ml beaker was added 54.0 g of deionized water and with moderate mixing, 1.3 g of Avicel PC 611 (FMC) Deveraux was slowly sifted in and homogenized for 10 minutes at 10,000 rpm. Into the mixture was then added 0.6 g of Keltrol CG SFT and which was also followed by homogenization for 10 minutes at 10,000 rpm and deaeration with vacuum.

The contents of the second beaker were added to the first beaker with moderate mixing. A premix of 1.0 g of Isopropyl Myristate NF (Inolex), and 0.01 g of Lycopene (OriStract LP) was added to the main batch with moderate mixing. The following were slowly added sequentially and with moderate mixing 10 minutes between additions: 2.0 g of Euxyl PE 9010 (Schuke & Mayr), 0.2 g of Anthemus Nobilis (Chamomile) Extract (ACTIVE Organics), 0.2 g of Salix Nigra (Willow) Bark Extract (Nab Willow Bark extract #127720 Arch), and 2.0 g of Botanileuca TT (Botanigenics) DD Chemco, The batch was then deaerated with vacuum and homogenization for 5 minutes at 5,000 rpm.

The resulting serum was stable at all conditions for at least 2.5 months and had 14% azelaic acid, 2% salicylic acid and had a pH of approximately 4.7-5.3.

Example 4

A total of 60 subjects with acne vulgaris participated in a clinical trial designed to demonstrate the safety and efficacy of the pharmaceutical compositions of the present invention. Approximately half of the participating subjects also presented with some degree of post-inflammatory hyperpigmentation.

The enrolled subjects were seen and evaluated at least once or twice weekly upon enrollment, and thereafter followed on a weekly or bi-weekly basis for up to twelve weeks to objectively evaluate the efficacy of the pharmaceutical compositions using digital imaging of the treated areas with a stereotactic face detection device (Canfield Scientific). Each subject was supplied the pharmaceutical composition of the present invention (14% azelaic acid and 2% salicylic acid) in either an emulsion or serum form and instructed to apply the composition twice daily after washing the affected area with a mild cleanser.

After having completed at least approximately four weeks of treatment, the subjects were provided a survey soliciting subjective information with respect to their dermatological disorder, adverse reactions, the appearance of their skin and the perceived efficacy of the pharmaceutical composition. Approximately 98% of the respondents indicated that they observed an immediate reduction in blemish size following the initiation of therapy with the supplied pharmaceutical composition. Approximately 97% of the respondents indicated that they observed a reduced incidence of inflammation and redness following treatment. Approximately 92% of the respondents indicated a reduction in new breakouts during treatment, while approximately 97% observed a smoother, moisturized and healthier texture of their skin following treatment.

In addition to a reduction in the presence of acne lesions, hyperpigmentation and acne scarring was also observed. No serious adverse reactions were observed or otherwise reported to the investigators during the investigation.

The foregoing therefore provides that the compositions of the present invention provide an effective therapy for the treatment of acne and PIH, and in particular novel topical therapies that improve symptoms in a safe, rapid and effective manner.

What is claimed is:

1. A stable topical pharmaceutical composition in the form of an emulsion, the emulsion comprising an aqueous phase and an oil phase,
wherein the aqueous phase comprises a tripartite complex,
wherein the tripartite complex consisting of L-arginine, azelaic acid and salicylic acid,
wherein the emulsion further comprises one or more unsolubilized salts dispersed therein and selected from the group consisting of an unsolubilized, micronized L-arginate salt of salicylic acid, and an unsolubilized, micronized L-arginate salt of azelaic acid, and
wherein the unsolubilized salts stabilize the emulsion by preventing the oil phase and the aqueous phase from coalescing.

2. The stable topical pharmaceutical composition of claim 1, wherein the L-arginine of the complex is an L-arginine alkyl ester.

3. The stable topical pharmaceutical composition of claim 1, wherein the L-arginine of the complex is an L-arginine ethyl ester.

4. The stable topical pharmaceutical composition of claim 1, wherein the composition is in the form of an oil, serum, ointment, cream, lotion, gel, shampoo, a saturated pad, a spray or a cleanser.

5. The stable topical pharmaceutical composition of claim 1, wherein the aqueous phase comprises the unsolubilized, micronized L-arginate salt of salicylic acid and the unsolubilized, micronized L-arginate salt of azelaic acid.

6. The stable topical pharmaceutical composition of claim 2, wherein the L-arginine alkyl ester enhances the transdermal absorption of the azelaic acid and the salicylic acid.

7. The stable topical pharmaceutical composition of claim 1, wherein the composition remains stable for at least 2 years upon storage at 37° C.

8. A method of treating a subject with a dermatological disorder, wherein the method comprises topically administering to a subject the stable topical pharmaceutical composition of claim 1 and wherein the dermatological disorder is selected from the group consisting of post-inflammatory hyperpigmentation (PIH), low skin hydration, excess sebum production and acne vulgaris.

9. A method of treating a dermatological disorder, wherein the method comprises topically administering to a subject affected with the dermatological disorder a pharmaceutical composition comprising an emulsion, wherein the emulsion comprises an aqueous phase and an oil phase, wherein the tripartite complex consisting of L-arginine, azelaic acid and salicylic acid,
wherein the emulsion further comprises one or more unsolubilized salts dispersed therein and selected from the group consisting of an unsolubilized, micronized L-arginate salt of salicylic acid, and an unsolubilized, micronized L-arginate salt of azelaic acid, and wherein the unsolubilized salts stabilize the emulsion by preventing the oil phase and the aqueous phase from coalescing; and wherein the wherein the dermatological disorder is selected from the group consisting of post-inflammatory hyperpigmentation (PIH), low skin hydration, excess sebum production and acne vulgaris.

10. The method of claim 9, wherein the pharmaceutical composition is in the form of an oil, serum, ointment, cream, lotion, gel, shampoo, a saturated pad, a spray or a cleanser.

11. The method of claim 9, wherein the composition is administered to the subject at least once daily.

12. The method of claim 9, wherein the symptoms of the dermatological disorder improve following administration of the pharmaceutical composition for 3 days.

13. A pharmaceutical composition in the form of an emulsion, the emulsion comprising an aqueous phase and an oil phase,
wherein the aqueous phase comprises a tripartite complex,
wherein the tripartite complex has a structure of formula (II):

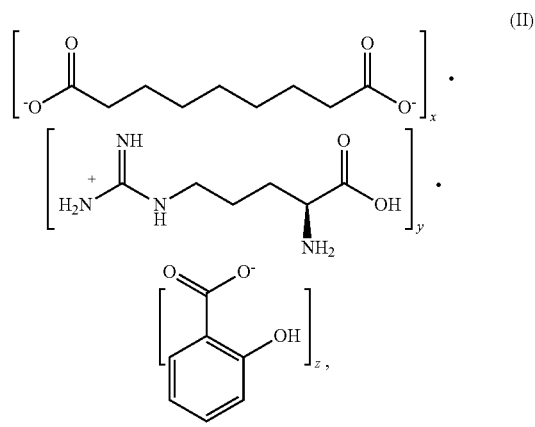

wherein x, y and z are each any positive integer,
wherein the emulsion further comprises one or more unsolubilized salts dispersed therein and selected from the group consisting of an unsolubilized, micronized L-arginate salt of salicylic acid, and an unsolubilized, micronized L-arginate salt of azelaic acid, and
wherein the unsolubilized salts stabilize the emulsion by preventing the oil phase and the aqueous phase from coalescing.

14. The pharmaceutical composition of claim 13, wherein x is one, y is four and z is two.

15. A method of treating a dermatological disorder, wherein the method comprises topically administering to a subject affected with the dermatological disorder the pharmaceutical composition of claim 13 and wherein the dermatological disorder is selected from the group consisting of post-inflammatory hyperpigmentation (PIH), low skin hydration, excess sebum production and acne vulgaris.

16. The pharmaceutical composition of claim 1, wherein the tripartite complex has the structure of formula (II):

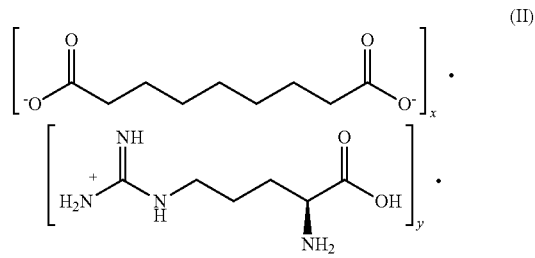

-continued
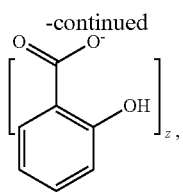
wherein x, y and z are each any positive integer.
* * * * *